United States Patent
Mooney et al.

(10) Patent No.: US 9,012,712 B1
(45) Date of Patent: Apr. 21, 2015

(54) ADSORPTION OF ACID GASES

(71) Applicant: BASF Corporation, Florham Park, NJ (US)

(72) Inventors: Dana Mooney, Natchez, MS (US); William Dolan, Yardley, PA (US); Gerald Rzeczkowski, Natchez, MS (US); Dennis Reinertsen, Hackettstown, NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 14/132,163

(22) Filed: Dec. 18, 2013

(51) Int. Cl.
*C07C 7/12* (2006.01)
*C10L 3/10* (2006.01)
*C10G 25/00* (2006.01)

(52) U.S. Cl.
CPC .............. *C10L 3/103* (2013.01); *C10G 25/003* (2013.01); *C07C 7/12* (2013.01)

(58) Field of Classification Search
None
See application file for complete search history.

(56) References Cited

U.S. PATENT DOCUMENTS

| 4,364,858 A | 12/1982 | Goodboy |
| 4,835,338 A | 5/1989 | Liu |

*Primary Examiner* — Tam M Nguyen
(74) *Attorney, Agent, or Firm* — Elizabeth Pietrowski

(57) ABSTRACT

An adsorption process is disclosed for removal of acid gas contaminants from a liquid or gas which comprises providing an activated alumina adsorbent which is impregnated with a compound selected from the group consisting of one or more alkali metal compounds, one or more alkaline earth metal compounds, or a mixture of such compounds; contacting the liquid or gas containing acid gas contaminants with the activated alumina adsorbent to adsorb enough acid gas contaminant in the liquid or gas to lower the contaminant content of the liquid or gas, the alumina adsorbent being formed from agglomerated calcined alumina powder and provided with a mercury pore volume of pores greater than 500 angstroms at least 0.10 cc/g.

25 Claims, No Drawings

ADSORPTION OF ACID GASES

FIELD OF THE INVENTION

This invention relates to the removal of acid gases from liquid or gas streams by selective adsorption of the acid gases on an alumina adsorbent.

BACKGROUND OF THE INVENTION

Acid gases are an undesirable impurity in materials such as, for example, petroleum hydrocarbons because several of these gases such as COS and $H_2S$ are a sulfur source and therefore a potential atmospheric pollutant. COS and $H_2S$ also act as an undesirable contaminant of industrial processes such as, for example, by poisoning of polymerization catalysts when the contaminant is present in petroleum-derived polymerizable olefins such as propylene. The acid gases may be introduced into such processes as a contaminant, initially present in the feedstock or they may be formed in the treating process as a result of the molecular sieve-catalyzed reaction of carbon dioxide with hydrogen sulfide or other sulfur compounds. For example, acid gases can be found in natural gas streams, and besides being a pollutant, acid gases such as COS, $H_2S$, $CO_2$, $CS_2$, $SO_2$, HCl, HF and HBr can be corrosive to natural gas pipelines, pipeline equipment, and other chemical processing apparatus.

Depending upon the process and the required purity of the product, COS levels in the starting material may be required to be reduced to below 1 part per million by weight (ppmw) and sometimes to levels below 100 part per billion by weight (ppbw). Concentration of COS in the range of a few ppmw cannot be separated efficiently from a petroleum feedstock such as propylene by fractional distillation because the boiling point of COS differs from propylene by only 3.4° C.

Khelghatian U.S. Pat. No. 3,315,003 teaches a process for removing COS from a hydrocarbon by first contacting the hydrocarbon with a liquid such as monoethanolamine which scrubs the hydrocarbon to remove acid gases such as $H_2S$ and $CO_2$ and part of the COS. The hydrocarbon is then distilled. After several subsequent distillations, the liquid bottom product is treated with a soda-lime to remove any remaining COS.

However, separation of COS by processes which involve distillation, in addition, are extremely costly due to the cost of energy to vaporize virtually all of the liquid. It is, therefore, desirable to provide other means for the removal of COS impurities from organic liquids.

It has also been proposed to remove COS from hydrocarbons by catalytic hydrolysis to form $H_2S$, for example, using alumina as a catalyst. Frevel et al U.S. Pat. No. 3,265,757 teaches the hydrolysis of COS contained in a liquid hydrocarbon by contacting a mixture of the liquid hydrocarbon and water, at a temperature of from 20 to 50° C., with a high surface area alkaline, active alumina containing from 0.15 to 3 wt. % of sodium or potassium. The patentees state that the hydrolysis reaction will not commence, however, if the alumina is bone dry. They suggest either moistening the alumina catalyst with ion-free water prior to the reaction or passing a mixture of ion-free water and the liquid hydrocarbon through the catalyst bed until a sufficient amount of water has built up on the alumina to permit the hydrolysis reaction to proceed. However, while this process does remove COS (by converting it to $H_2S$), it does not remove sulfur from the hydrocarbon, but merely changes the form of the sulfur compound which still must be subsequently removed from the hydrocarbon by another process step.

In a later patent dealing with the same type of reaction, Polleck et al U.S. Pat. No. 4,491,516 teach that the reaction rate for the hydrolysis of COS with water over alumina may be greatly increased if the ratio of water to COS ranges from 1 to 10 moles of water per mole of COS, preferably 1.5 to 6 moles of water per mole of COS, or about 30% of saturation of the hydrocarbon, whichever upper limit provides the lesser amount of water.

Brownell et al U.S. Pat. No. 4,455,446 teaches the removal of COS from propylene by hydrolysis over a catalyst comprising platinum sulfide on alumina. The patentees state that the hydrolysis reaction may be carried out in either the gaseous or liquid phase with a temperature of 35° to 65° C. used for the liquid phase. An amount of water at least double the stoichiometric amount of the COS to be hydrolyzed must also be present.

Harris et al U.S. Pat. No. 4,391,677 describe a process for desulfurizing a butene-1 rich stock containing sulfurous impurities such as $H_2S$, COS, and $CH_3SH$. The process comprises passing the feed stream through a desulfurization zone maintained under desulfurization conditions and containing a charge of at least one desulfurization medium capable of adsorbing, absorbing, or converting $H_2S$, COS, and $CH_3SH$ to high boiling sulfurous compounds. The thus-treated feed stream, now essentially free from $H_2S$, COS, and $CH_3SH$, is then passed to a distillation zone, and recovered as a bottom product as a butene-2 rich stream containing high boiling sulfurous compounds. The desulfurization zone comprises a bed of activated alumina followed by a bed of zinc oxide. The activated alumina is said to hydrolyze COS in the presence of 20 to 1000 ppm of water to $H_2S$ and partially to remove $H_2S$ and methyl mercaptan. The zinc oxide is said to remove all the $H_2S$ and methyl mercaptan not removed by the alumina bed.

COS has also been removed from liquid hydrocarbons by adsorption on a zeolite adsorbent. Collins U.S. Pat. No. 3,654,144 discloses removing COS by adsorbing it on a particular modified zeolite A adsorbent comprising an alkali metal cation form of zeolite A which has been ion-exchanged with alkaline earth metal cations, preferably calcium cations, to the extent of from 20 to about 100 equivalent percent.

Innes U.S. Pat. No. 4,098,684 describes the removal of COS and other sulfur compounds by passing them through a dual bed of zeolites comprising, respectively, a 13× molecular sieve, and a zeolite A sieve having a pore size of 4 Angstroms. The commercially available 13× zeolite is said to remove any $H_2S$ and mercaptans present. The capacity for COS adsorption by the 13× sieve is said to be small. The 13× zeolite is described as a three dimensional network with mutually connected intracrystalline voids accessible through pore openings which will admit molecules with critical dimensions up to 10 Angstroms and having the general chemical formula: $0.83.+-.0.05$ $Na_2O/1.00$ $Al_2O_3/2.48.+-.0.038$ $SiO_2$. The molecular sieve beds may be regenerated by passing a hot, substantially nonadsorbable, purge gas through the beds at a temperature of about 177° to 316° C.

While zeolite materials have thus been used as adsorbing agents to remove sulfurous compounds such as COS from liquids hydrocarbons, it has been found that zeolite, with its cage structure, has a low adsorption rate at ambient temperature and is, therefore, not practical for treating liquids at such temperatures.

It would, therefore, be highly desirable to provide a process for the removal of acid gases including sulfurous impurities such as COS from liquids or gases, preferably in the absence of water, using an alumina adsorbent having high adsorption characteristics yet capable of being regenerated without substantial loss of adsorption capability. Removal of acid gases other than COS from liquids or gases to minimal ppm levels using an alumina absorbent would also be desirable.

U.S. Pat. No. 4,835,338 to Liu provides an improved process for the removal of carbonyl sulfide from a liquid hydrocarbon by adsorption on an adsorption media comprising an activated alumina adsorbent followed by regeneration of the activated alumina after the adsorption capacity has been reached. The activated alumina adsorbent is pretreated with a compound selected from the class consisting of one or more alkali metal compounds, one or more alkaline earth metal compounds, or mixtures of any two or more of such compounds; then used to adsorb carbonyl sulfide from a hydrocarbon; and then regenerated by passing a gas through the adsorbent. Useful activated alumina is disclosed as a commercial product having a particle size range of from ¼ inch to 100 mesh (150 microns). In practice, the alumina particles are formed by agglomerating 5 micron alumina powders into the larger particles suitable for the adsorption process.

SUMMARY OF THE INVENTION

It is an object of this invention to provide an improved process for the removal of acid gases from liquids or gases, which comprises adsorbing the acid gases on an adsorption media comprising an activated alumina which has been previously treated with one or more alkali metal compounds, one or more alkaline earth metal compounds, or a mixture thereof. It has been found that if the alumina adsorbent is formed from agglomerated alumina powder and provided with a mercury pore volume after treatment with the alkali metal and/or alkaline earth metal compounds of at least 0.10 cc/g of pores greater than 500 angstroms, improved adsorbent capacity for acid gases is achieved.

DETAILED DESCRIPTION OF THE INVENTION

The invention comprises an improved process for removal of acid gases, such as above described including carbonyl sulfide (COS) from liquids or gases by adsorption on an activated alumina adsorbent. Regeneration of the adsorbent can be achieved and conducted when the capacity of the adsorbent has been reached. The activated alumina adsorbent used in the process of the invention comprises an activated particulate alumina having a particle size range of from about ¼" to about 100 mesh (U.S. Series). These particles are formed from agglomerated alumina powders having an average size of from about 1 to 10 microns. The alumina particles are formed with a total mercury pore volume of at least 0.45 cc/g, usually at least 0.50 cc/g, preferably at least 0.60 cc/g, more preferably, at least 0.70 cc/g.

The desired pore volume of the alumina particles can be achieved by several methods, including agglomerating alumina powders having an average size range of from about 1 to 4 microns. If larger alumina powders, e.g. above 4 microns are used, a burnout additive can be agglomerated with the powders. The burnout additive is removed and/or carbonized during subsequent calcination.

Starting materials suitable for the practice of the present invention include pseudoboehmite, gibbsite, bayerite and any other form of alumina which when properly treated yields adsorbents having a sodium oxide concentration of 0.10 to 2.5 wt. % (1100° C. calcined basis), an LOI (hydroxyl content determined by heating from 400° to 1100° C.) of 2.0 to 9.0 wt. %, and a surface area of 100 to 500 m²/g (BET).

The starting material of the present invention may have particles having a particle size of 75 microns or larger. These particles should be ground to a particle size of about 1-10 microns to achieve a particularly advantageous adsorbent. Any grinding technique known to those skilled in the art may be used.

Once the alumina starting material has an average particle size of approximately 1 to 10 microns, the alumina is rapidly activated by exposure to high temperature for a brief period of time. Methods for such rapid activation are well known in the art. One technique which has been found to be particularly useful is that described in U.S. Pat. No. 2,915,365. In accordance with this patented disclosure, alumina is injected into a stream of highly heated gases (e.g. air) at gas temperatures of greater than 300° C., such as 300° to 1000° C. The duration of contact between the alumina and the hot gas may be less than one minute, such as from a fraction of a second to several seconds, with two to three seconds being the preferred contact time. The alumina, once activated, is either in the gamma phase or an amorphous phase or a mixture thereof.

In a preferred embodiment of the present invention, the rapidly activated alumina is ball formed (agglomerated) in the presence of water and then reactivated by any of a number of methods known to those skilled in the art. One method which yields a good activated alumina is to expose the aged alumina to a temperature in the range of 300° to 800° C. for a period of 10 minutes to about four hours, with temperatures of 350° to 450° C. for 15 minutes to two hours being typical conditions. Proper final activation, like powder activation, is important in developing an adsorbent with low LOI, but high surface area.

In general, the burnout additive is a carbon-based material. Examples of burnout additives include sugars, starches, and lignin or grain flours such as wood, wheat, corn, rye, etc. Water soluble polymers such as polyethylene oxide, polyvinyl alcohol, etc., can also be used.

The activated alumina preferably is impregnated with one or more alkali metal compounds, one or more alkaline earth metal compounds, or a mixture thereof in an amount which may range from about 0.01 to about 15 wt. %, preferably from about 1.0 to about 8.0 wt. %, more preferably from about 2.0 to about 8.0 wt. % and, most preferably, from about 3.0 to about 6.0 wt. %, wherein the wt. % is measured as the percentage weight of the impregnated alkali metal or alkaline earth metal as oxide to the total weight of the impregnated alumina adsorbent. The alkali metal compound or alkaline earth metal compound preferably will comprise a material with a decomposable anion so that no undesirable other materials are left in the alumina after the impregnation. Examples of such alkali metal/alkaline earth metal compounds include, for example, the hydroxides, carbonates, and nitrates of sodium, potassium, lithium, calcium, and magnesium.

The activated alumina may be impregnated by the alkali metal/alkaline earth metal compound by soaking the activated alumina for at least about 5 minutes up to 1 hour or longer in an aqueous solution containing the dissolved alkali metal/alkaline earth metal compound and then drying the impregnated alumina and reactivating at 300° to 450° C. for one to two hours. More than one cycle of impregnation and drying may be used, if desired. The compound may also be applied to the activated alumina by spraying or the like, if desired.

The impregnated and reactivated alumina adsorbent is improved if the treated adsorbent has a total mercury pore volume of at least 0.4 cc/g, typically at least 0.45 cc/g, preferably at least 0.5 cc/g and, more preferably, at least 0.55 cc/g. Further, vast improved adsorption of acid gasses is achieved if the impregnated and reactivated alumina adsorbent has a pore volume of pores greater than 500 angstroms of at least 0.1 cc/g, typically at least 0.15 cc/g, preferably at least 0.30 cc/g and, more preferably at least 0.40 cc/g.

The improved activated alumina adsorbents are capable of treating a gas or liquid, containing an impurity concentration of acid gas of as much as 200 ppm and reducing the concentration down to below 1 ppm. Since the removal of COS or the other acid gases from a liquid or gas containing such impurities therein is principally via adsorption, the presence or absence of any specific amounts of moisture is not critical to the operation of the process. However, since it has been found that the capacity of the adsorbent for acid gases varies inversely with the amount of water present, it is preferred to operate with as little water present as possible. It should also be noted that no water need be present for the adsorption process to operate successfully.

In a preferred embodiment, the acid gas impurity is removed from a liquid or gaseous hydrocarbon stream. The hydrocarbon stream to be purified may be first passed through a drying bed such as a molecular sieve or silica or the like to remove most if not all of the moisture present prior to passing the hydrocarbon stream through the adsorbent to avoid the reduction in adsorption capacity just discussed above. Contaminants to be removed by the adsorbents of this invention are acid gases or acid gases dissolved in liquids comprising COS, $H_2S$, $CO_2$, $CS_2$, $SO_2$, HCl, HF, HBr, with the main constituents of the streams consisting predominately of ethylene, propylene, butane, or mixtures of various olefins, natural gas, synthesized gas derived from biomass, hydrogen, nitrogen, or air. The main constituent of the stream can be either in a gaseous or liquid form.

If moisture is present in the hydrocarbon stream, some of the acid gases may be converted by hydrolysis to other reaction products, which may then be adsorbed onto the alkali metal-impregnated activated alumina adsorbent. Such adsorbed reaction products may then be removed, along with the adsorbed acid gas, upon subsequent regeneration of the adsorbent, if desired.

The adsorption process may be carried out at ambient temperature, although temperatures of from 15° to 100° C. may be used if convenient, e.g., if the contaminated liquid or gas is at this temperature from previous processing, it need not be heated or cooled prior to passing through the adsorbent.

The adsorption may be advantageously carried out in a packed column although any other convenient form of maintaining contact between the adsorbent and the acid gas-contaminated feed may be employed such as a slurry process. The flow rate of the feed through the adsorbent should be sufficiently slow to permit a sufficient contact time for the desired adsorption of the acid gas from the feed onto the alkali metal/alkaline earth metal-impregnated activated alumina to occur. The actual amount of contact time will vary with the particle size of the adsorbent.

The adsorption capacity of the alkali metal/alkaline earth metal-impregnated activated alumina adsorbent for sulfur-containing acid gases is determined by monitoring the sulfur content of the effluent from the adsorbent. Prior to reaching its adsorption capacity, the effluent will contain less than 1 ppm sulfur. After such monitoring indicates that the capacity of the adsorbent has been reached, i.e., by a rise in the sulfur content of the effluent, the adsorbent may be regenerated by passing a heated gas such as air, hydrocarbon gases, nitrogen or other inert gases through the adsorbent. The heated gas is preferably heated to a temperature from about 100° to 300° C., more preferably about 150° to 250° C., and most preferably about 250° C., and passed through the adsorbent at a rate of about 1 to 10 cc/min. until a substantial amount of the sulfur adsorbed thereon is removed. A substantial amount is about 40 wt. % or higher of the adsorbed sulfur. This can easily be determined by analyzing the amount of residual sulfur in the adsorbent. The direction of flow of the regenerating gas through the adsorbent may be either in the same direction as the feed flow, e.g., when the adsorbent is packed in a column, or the regenerating gas may be passed through the adsorbent in a direction counter to the normal flow of feed there through. Adsorption capacity for other acid gases may be determined by known means for measuring the other anionic species, e.g. Cl, F, etc.

The following examples will serve to better illustrate the process of the invention.

EXAMPLES

COS adsorbents were prepared as described below. The adsorbents were placed in respective beds and subjected to test conditions of rapid aging and breakthrough testing as described below.

Test Conditions

Rapid Aging (Rapid Regeneration)

Each bed was loaded with 78 grams of the adsorbent. The adsorbent beds were then subjected to a cycle of adsorption, regeneration and cooling. The three steps were repeated a total of 35 times. At the end of the 35th cycle, each bed was heated for an additional 2 hours with a flow of 0.5 slpm at 270° C. and then cooled to ambient temperature. During the adsorption step of rapid aging, the bed was fed 450 ppm of COS in nitrogen at a flow of 8.7 slpm at temperature of 35° C. and pressure of 80 psia for 35 minutes. During the regeneration step the bed was at a pressure of 15 psia and a temperature of 270° C. with a flow of 0.5 slpm nitrogen feed counter current to the adsorption step. During the cooling step of rapid aging the bed was at a pressure of 15 psia and a temperature of 35° C. with a flow of 0.5 slpm nitrogen feed counter current to the adsorption step.

Breakthrough Test

After the beds completed the rapid aging test, a breakthrough test was completed. During this test the beds were fed 75 ppm COS in nitrogen at a flow of 6.45 slpm and a temperature of 35° C. The beds were run for a time such that the COS at the outlet of the bed reached the feed condition.

Example 1

Beads were prepared mixing 15 grams of pore former with 85 grams of flash calcined alumina powders of approximately 5 micron in size. The material was formed into beads using a pan agglomeration technique and screened to a 7×14 Tyler mesh. The material was then calcined at a temperature of 842° F. for 2 hours. The activated material was then dipped in a solution of 9.8 wt % NaOH for 20 minutes and the material again activated at a temperature of 572° F. and a time of 2 hours. The resulting material had a 6 wt % $Na_2O$ content.

Example 2

The material from Example 1 was rapidly aged as described in the Rapid Aging protocol. After aging, the material from Example 1 was then tested in the breakthrough test. The material broke through to 2 ppm of COS in 640 minutes and 25 ppm of COS in 880 minutes.

Example 3

Beads were prepared by grinding alumina powders of approximately 5 microns to a powder of approximately 1.5 microns. The alumina powder was formed into beads using a pan agglomeration technique and screened to a 7×14 Tyler mesh. The beads were then calcined at a temperature of 700° F. for a time of 2 hours. The activated beads were then dipped in a solution of 9.8 wt % NaOH for 20 minutes and the beads again activated in a pan activator at a temperature of 572° F. for a period of 2 hours. The resulting material had a 6 wt % $Na_2O$ content.

Example 4

The material from example 3 was rapidly aged as described in the Rapid Aging protocol. After aging, the material from Example 3 was then tested in the breakthrough test. The material broke through to 2 ppm of COS in 640 minutes and 25 ppm of COS in 880 minutes.

Example 5

Control

Beads were prepared by flash activating approximately 5 micron alumina powder and then forming the activated powder into beads using a pan agglomeration technique. The beads were screened to a 7×14 Tyler mesh. The material was then calcined at a temperature of 760° F. for a time of 2 hours. The activated material was then dipped in a solution of 9.8 wt % NaOH for 20 minutes and the material again activated in a pan activator at a temperature of 572° F. and a time of 2 hours. The resulting material had a 4% wt % $Na_2O$ content.

Example 6

Control Result

The control material from Example 5 was rapidly aged as described in the Rapid Aging protocol. It was then tested in the breakthrough test. The control material broke through to 2 ppm of COS in 250 minutes and 25 ppm of COS in 497 minutes.

Example 7

Control

Beads were prepared by flash activating approximately 5 micron alumina powder and then forming into beads using a pan agglomeration technique. The beads were screened to a 7×14 mesh. The material was then calcined at a temperature of 760° F. and time of 2 hours. The activated material was then dipped in a solution of 12 wt % NaOH for 20 minutes and the material again activated at a temperature of 572° F. and a time of 2 hours. The resulting material had a 6 wt % $Na_2O$ content.

Example 8

Control Result

The control material from Example 7 was rapidly aged as described in the Rapid Aging protocol, and then tested in the breakthrough test. The material broke through to 2 ppm of COS in 300 minutes and 25 ppm of COS in 500 minutes.

Example 9

The pore volume of the material from Example 1 was measured prior to dipping by mercury pore symmetry using a Micromeritics instrument. The total pore volume of the material was 0.63 cc/g. Pore volume of pores greater than 500 Angstroms was 0.61 cc/g.

Example 10

The pore volume of the material from Example 3 was measured prior to dipping by mercury pore symmetry using a Micromeritics instrument. The total pore volume of the material was 0.72 cc/g. Pore volume of pores greater than 500 Angstroms was 0.29 cc/g Example 11

The pore volumes of the control materials from Examples 5 and 7 were measured prior to dipping by mercury pore symmetry using a Micromeritics instrument. The total pore volume of each material was 0.38 cc/g. Pore volume of pores greater than 500 Angstroms was 0.11 cc/g.

TABLE 1 below summarizes the results of the tests described above.

TABLE 1

| Example No. | Aged 35 Cycles COS 2 ppm Time (min) | Aged 35 Cycles COS 25 ppm Time(min) | Total PV Starting Bead (cc/g) |
|---|---|---|---|
| 1 | 640 | 880 | 0.63 |
| 3 | 638 | 880 | 0.72 |
| 5 | 250 | 497 | 0.38 |
| 7 | 300 | 500 | 0.38 |

Example 12

The materials of Examples 1, 3, 5 and 7 were measured for pore volume after dipping and activation. The material of Example 1 after dipping and activation had a total pore volume of 0.56 g/cc and for pores greater than 500 Angstroms had a pore volume of 0.15 g/cc. The material of Example 3 after dipping and activation had a total pore volume of 0.59 g/cc and for pores greater than 500 Angstroms had a pore volume of 0.41 g/cc. The material of control Example 5 after dipping and activation had a total pore volume of 0.36 g/cc and for pores greater than 500 Angstroms had a pore volume of 0.07 g/cc. The material of control Example 7 after dipping and activation had a total pore volume of 0.34 g/cc and for pores greater than 500 Angstroms had a pore volume of 0.04 g/cc.

| | Total PV cc/g | 500 Å and greater cc/g |
|---|---|---|
| Example 1 | 0.56 | 0.15 |
| Example 3 | 0.59 | 0.41 |
| Example 5 | 0.36 | 0.07 |
| Example 7 | 0.34 | 0.04 |

The invention claimed is:

1. A process for removal of an acid gas contaminant from a liquid or gas by adsorption which comprises:
    contacting the liquid or gas containing acid gas contaminant with an activated alumina adsorbent impregnated with from 0.1 to 15 wt. % of a metal compound, based on the weight ratio of the metal as oxide in said compound to said impregnated adsorbent, said metal compound selected from the group consisting of one or more alkali metal compounds, one or more alkaline earth metal compounds, or a mixture of such compounds, to adsorb the acid gas contaminant in the liquid or gas for a period of time sufficient to lower the acid gas contaminant content of the liquid or gas; and wherein said impregnated alumina adsorbent has a mercury pore volume of pores greater than 500 angstroms of at least 0.10 cc/g.

2. The process of claim 1, wherein said impregnated metal compound comprises from about 1.0 to about 8.0 wt. % as metal oxide relative to said impregnated adsorbent.

3. The process of claim 2, wherein said impregnated metal compound comprises from about 2.0 to 6.0 wt. % as metal oxide relative to said impregnated adsorbent.

4. The process of claim 1, wherein the metal in said metal compound impregnated in said activated alumina adsorbent consists essentially of sodium.

5. The process of claim 1, wherein said liquid or gas is a hydrocarbon stream.

6. The process of claim 5, wherein said hydrocarbon stream is an olefin stream.

7. The process of claim 5, wherein said hydrocarbon stream is a natural gas stream.

8. The process of claim 1, wherein said alumina adsorbent is formed by agglomerating a calcined alumina powder having an average particle size from 1 to 10 microns.

9. The process of claim 1, wherein said alumina adsorbent is formed by agglomerating a calcined alumina powder having an average particle size of from 1 to 4 microns.

10. The process of claim 8, wherein said calcined alumina powder has an average particle size of from greater than about 4.0 microns to 10 microns and is agglomerated with a burnout additive into beads, said beads being calcined to remove said additive.

11. The process of claim 10, wherein said burnout additive is a carbon-based material.

12. The process of claim 6, wherein said olefin is ethylene and/or propylene.

13. The process of claim 1, wherein said impregnated adsorbent has an overall mercury pore volume of at least 0.40 cc/g.

14. The process of claim 1, wherein said impregnated adsorbent has an overall mercury pore volume of at least 0.5 cc/g.

15. The process of claim 1, wherein said impregnated absorbent has a mercury pore volume of pores greater than 500 angstroms of at least 0.15 cc/g.

16. The process of claim 1, wherein said impregnated absorbent has a mercury pore volume of pores greater than 500 angstroms of at least 0.30 cc/g.

17. The process of claim 1, comprising regenerating the activated alumina adsorbent to remove a substantial amount of acid gas contaminant absorbed thereon.

18. The process of claim 17, wherein said activated alumina adsorbent is regenerated by passing a heated gas through the absorbent.

19. The process of claim 1, wherein said acid gas is selected from the group consisting of COS, $H_2S$, $CO_2$, $CS_2$, $SO_2$, HCl, HF and HBr.

20. The process of claim 19, wherein said acid gas is COS, $H_2S$, $CS_2$ or $SO_2$.

21. The process of claim 8, wherein said alumina adsorbent has a total mercury pore volume of at least 0.45 cc/g prior to impregnation.

22. The process of claim 8, wherein said alumina adsorbent has a total mercury pore volume of at least 0.5 cc/g prior to impregnation.

23. The process of claim 8, wherein said alumina adsorbent has a total mercury pore volume of at least 0.6 cc/g prior to impregnation.

24. The process of claim 1, wherein said liquid or gas is a synthetic liquid or gas formed from biomass.

25. The process of claim 24, wherein said acid gas contains sulfur.

* * * * *